(12) United States Patent
Hoyt

(10) Patent No.: US 6,665,072 B2
(45) Date of Patent: Dec. 16, 2003

(54) INSTANTANEOUS DUAL BAND FLUORESCENCE DETECTION SYSTEMS

(75) Inventor: Clifford C. Hoyt, Needham, MA (US)

(73) Assignee: Cambridge Research & Instrumentation Inc., Woburn, MA (US)

(*) Notice: Subject to any disclaimer, the term of this patent is extended or adjusted under 35 U.S.C. 154(b) by 173 days.

(21) Appl. No.: 09/793,853

(22) Filed: Feb. 26, 2001

(65) Prior Publication Data

US 2001/0046050 A1 Nov. 29, 2001

Related U.S. Application Data

(60) Provisional application No. 60/184,844, filed on Feb. 25, 2000.

(51) Int. Cl.[7] .............................................. G01N 21/25
(52) U.S. Cl. ................................................... 356/417
(58) Field of Search ............................. 356/317–318, 356/416–418, 364–370; 250/458.1, 459.1, 461.1; 422/82.05, 82.08; 436/172

(56) References Cited

U.S. PATENT DOCUMENTS

| | | | |
|---|---|---|---|
| 4,352,558 A | 10/1982 | Eisert | 356/39 |
| 5,943,129 A | 8/1999 | Hoyt et al. | 356/318 |
| H1843 H | 3/2000 | Bur et al. | 250/458 |
| 6,160,618 A | 12/2000 | Garner | 356/318 |
| 6,396,053 B1 * | 5/2002 | Yokoi | 250/234 |

FOREIGN PATENT DOCUMENTS

WO    WO 98/38542    9/1998

OTHER PUBLICATIONS

Journal of Biomolecular Screening, vol. 5, No. 5 (2000), pp. 297–306, "*Fluoescence Polarization and Anisotropy in High Throughput Screening: Perspectives and Primer*", John C. Owicki.

International Search Report, May 25, 2001.

* cited by examiner

*Primary Examiner*—Tu T. Nguyen
(74) *Attorney, Agent, or Firm*—Cohen, Pontani, Lieberman & Pavane

(57) ABSTRACT

An apparatus for performing fluorescence detection of two or more biochemical probes and/or fluorescence measurement of fluorescence intensity at two or more spectral bands of light emitted from at least one sample spot is disclosed. The apparatus simultaneously directs emitted fluorescent light from multiple probes and/or at multiple spectral bands to different spots on a single pixelated detector.

34 Claims, 10 Drawing Sheets

INSTANTANEOUS DUAL BAND FLUORESCENCE DETECTION SYSTEMS

PRIORITY CLAIM

Priority under 35 U.S.C. §119(e) is claimed from U.S. Provisional Application Ser. No. 60/184,844, filed on Feb. 25, 2000.

BACKGROUND OF THE INVENTION

1. Field of the Invention

The invention is directed toward instrumentation for biochemical assays, more particularly assays using fluorescence detection with two or more labels in the experiment; or assays requiring a ratiometric measurement of fluorescence intensity at two spectral bands.

2. Description of the Related Art

Fluorescence assays that use multiple probes typically require measuring the fluorescence emission levels in two spectral bands, corresponding to the probes involved. Similarly, one may look in two bands to detect shifts in the spectrum of a single probe, if its emission spectrum is sensitive to environment. Examples of such probes include Indo, for pH sensing; or Acridine Orange to sense binding to RNA. In these cases, one wishes to use spectral ranges whose flux levels will be most sensitive to the spectral shift.

In such measurements, one often seeks to compare the flux in levels between the bands with high precision. In an assay looking for spectral shifts in a single probe, the ability to take precise ratios sets the detection limit for how small of a spectral shift can be detected. In dual-probe experiments, measuring the ratio precisely is valuable as well.

Existing fluorescence readers offer one the means to choose what spectral band will be measured, so it is possible to perform a dual band measurement simply by reading the sample twice in series. However, this is undesirable for several reasons. First, it takes twice as long as a single-band measurement, which can result in sample aging. Second, fluorescent probes exhibit photobleaching so the second reading is diminished in intensity, which distorts the measured ratio of fluxes. Finally, lamp flicker and drift are a significant source of noise in fluorescent measurements, and will degrade the measurement of flux ratios between bands.

Some instruments incorporate two or more detectors viewing the same sample simultaneously. These divide the beam according to wavelength band using partial-mirrors or dicroic elements to split of a sample portion to each detector. This approach is superior in the sense that it affords a higher throughput by reading both bands at once; and since the bands are measured under identical illumination conditions, a ratio of the two is not affected by lamp flicker or drift. However, such instruments bear a cost burden due to the need for two detectors and readout electronics, plus beam-splitters. This cost burden becomes even more significant if one wishes to make an imaging system of this type, using two pixelated detectors such as CCD detectors. In addition to the higher cost of the detectors and readout electronics, the two detectors need to be carefully registered in order that one can relate the image elements seen at a particular pixel on a first detector with a given pixel at the other detector. This registration must be handled carefully and while the approach is simple in theory, building such an instrument in practice tends to be demanding.

There is another problem with existing multiband fluorescence instruments. The use of dielectric filters at non-normal incidence to sample the beam, or indeed anywhere in the instrument, can lead to systematic spectral and polarization errors. In general, the off-axis reflection and transmission properties of dielectric film are different for the S- and P-state of polarization. Simply put, one observes a different spectral band in the S-polarization than one does in the P-polarization. In some cases, the difference is not significant because the spectral width of the overall measurement is determined by some other element in the system, such as a normal-incidence filter elsewhere in the system.

In practice, problems are most likely present when one wishes to observe bands that are spectrally adjacent, or where one band is spectrally close to the excitation wavelength. Yet dual-probe assays typically use one probe with a long Stokes shift, and one with a short Stokes shift (i.e. spectrally close to the excitation wavelength). Such samples are not measured accurately by an instrument that uses dielectric filters to split off the beam to multiple detectors. Thus the deficiencies of the prior art instruments are most likely to be germane, precisely when utilizing their dual-band readout capability to read dual-probe assays.

Such a dual-detector approach also would be less than optimal for measuring fluorescence polarization, due to the polarization sensitivity of the instrument. All existing fluorescence polarization instruments operate on a single band at the same time, so they suffer the throughput and noise penalties discussed above in connection with all single-band instruments.

An instrument described in U.S. Pat. No. 6,160,618 issued to Garner uses an imaging spectrometer to obtain a complete spectrum of the fluorescent emission by means of a dispersive element such as a grating or prism. There are several limitations to this instrument. In addition to the complexity of this approach, the instrument can only collect light from a small region corresponding to the image of the spectrometer slit projected on the sample. Thus its sensitivity is relatively low compared to instruments that can illuminate, and collect light from, extended regions such as sample spots or microtitre plate wells. Further, the efficiency of gratings and prisms depends upon polarization state, which renders a dispersive instrument inherently ill-suited for fluorescence polarization assays Thus there is no instrument for fluorescence assay measurement which at once provides for simultaneous readout of two bands for high throughput and low-noise assessment of band ratios; with the economy of a single detector; or with high accuracy when used with short Stokes-shift probes or for fluorescence polarization measurements.

SUMMARY OF THE INVENTION

It is an object of the present invention to provide for an ultra-high-throughput measurements at two bands without the need for multiple detectors that add cost or tilted dielectric filters that degrade accuracy.

It is a further object of the present invention to enable making dual-band ratio measurements with high precision suitable for use with Fluorescence Resonance Energy Transfer (FRET) potentiometric assays or environmentally-sensitive probes.

It is a further object of the present invention to enable performing dual label fluorescence polarization assays to detect single nucleotide polymorphism (SNP).

It is a further object of the present invention 1 to provide for fluorescence polarization measurements with high accuracy, for either a single probe or for two probes at once.

It is yet another object of the present invention to provide for reading more than one sample region at a time, to further increase the throughput.

It is yet another object of the present invention to achieve this in a compact, economical design which has no moving parts.

These and other objects are achieved by the present invention, which provides a system and method for separating fluorescent light emitted from a spot on a sample into multiple spots according to wavelength and, in some embodiments, according to polarization state when emitted by the sample as well. The resultant spots are directed to a multi-pixel detector where their flux is measured.

In one illustrative system, the sample is illuminated with a laser spot, and the fluorescence emitted from the spot is first separated into two spots according to polarization state using a double-refractive element. Each of these passes through a birefringent network which changes the state of polarization to its complement, or not, depending on its wavelength. A second double-refractive element further splits each of the two spots by polarization, which now corresponds to wavelength in a predetermined way; to yield four spots, separated according to wavelength and polarization state at the sample.

This arrangement can be used for dual band fluorescence assays of all kinds. It is ideal for dual-probe fluorescence polarization assays, since it simultaneously captures all ratios of intensity and of wavelength, eliminating lamp drift between measurements as a source of error. Blocking of the excitation source is achieved by a conventional long-pass filter, a holographic notch filter, or other blocking element, as is known in the art of instrument design. It is further possible to use bandpass or multiband filters to further define the spectral bands, which are primarily set by the birefringent network.

In another illustrative system, the second double-refraction element is replaced by a linear polarizer, and two spots corresponding to different wavelengths are presented to different regions of the detector.

It is possible to put a polarization rotator before the first double-refractive element, and thus change which spot at the detector corresponds to what polarization at the sample. It is also possible to put a polarization rotator between the first and second double-refractive elements, and thus to change which spot at the detector corresponds to what wavelength. This can be useful in instrumental calibrations and the like. The polarization rotators can be liquid crystal cells, so interchanging spot locations in this way is rapid and does not require any moving parts.

It is possible to put a pixelated polarization rotator in the path of just one of the two spots at the point between the first and second double-refractive element, and thus to interchange the location of only two of the spots at the detector. In this way one can arrange the spots so that e.g. all spots with a given wavelength are adjacent, or all spots of a given polarization are adjacent. This enables high-speed readout when only polarization information, or only wavelength information, is of interest.

Since all spots are delivered to a single image plane, they may be read out with a single pixelated detector, such as a CCD, linear photodiode array, or pixelated Photomultiplier tube (PMT). In versions that use a double-refractive element rather than a linear polarizer as the second element, all the fluorescent flux is utilized for the measurement and high optical efficiency can be attained.

It is possible to make all these measurements for plural points on the sample, by choice of suitable illumination optics that excite more than one sample region at once. This multiplies the measurement throughput by the number of illumination spots, for high throughput and ultra-high throughput applications. Using diffractive optical elements it is possible to produce 16 spots or more at the sample, from a single laser source.

This invention is valuable when precise dual-label fluorescence assays and fluorescence polarization assays are needed, as in pharmacogenomics. It is also valuable in taking emission intensity ratios, as in Fluorescence Resonance Energy Transfer (FRET) and membrane potential experiments.

The ability to obtain dual-band spectral data without a significant burden in cost, throughput, or optical efficiency, makes it practical to obtain a second band for purposes other than imaging two probes. For example, the instrument may be set to image a primary band corresponding to the probe of interest, and a secondary band corresponding to background fluorescence. Having an in-situ measure of background fluorescence at the secondary band, together with some knowledge of the spectral distribution of background fluorescence, enables improved background correction at the primary (probe) band. Thus even single-probe measurements can be improved by the present invention.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

The following figures are all intended to be schematic in nature, and like elements are denoted by the same number.

DETAILED DESCRIPTION OF THE PRESENTLY PREFERRED EMBODIMENTS

Throughout the following, one state of polarization is termed h and its complement is v. These need not be literally horizontal and vertical, but either h or v must correspond to the major axis of the state of polarization used to excite the sample in any given measurement.

The term spectral band is used to refer to a set of wavelengths of light, either in the visible, infrared, or ultraviolet spectral region. The term probe is used to describe a substance that emits fluorescent light when optically excited, which enables measuring one or more properties of a sample, through observation of the brightness, spectral distribution, polarization, or combinations thereof, of the fluorescent emission. The term spot is used to describe a spatial region on the sample that is optically excited, as well as to describe the rays emanating from that region as they propagate through the optical system and form images thereof at a detector.

Figure 1:
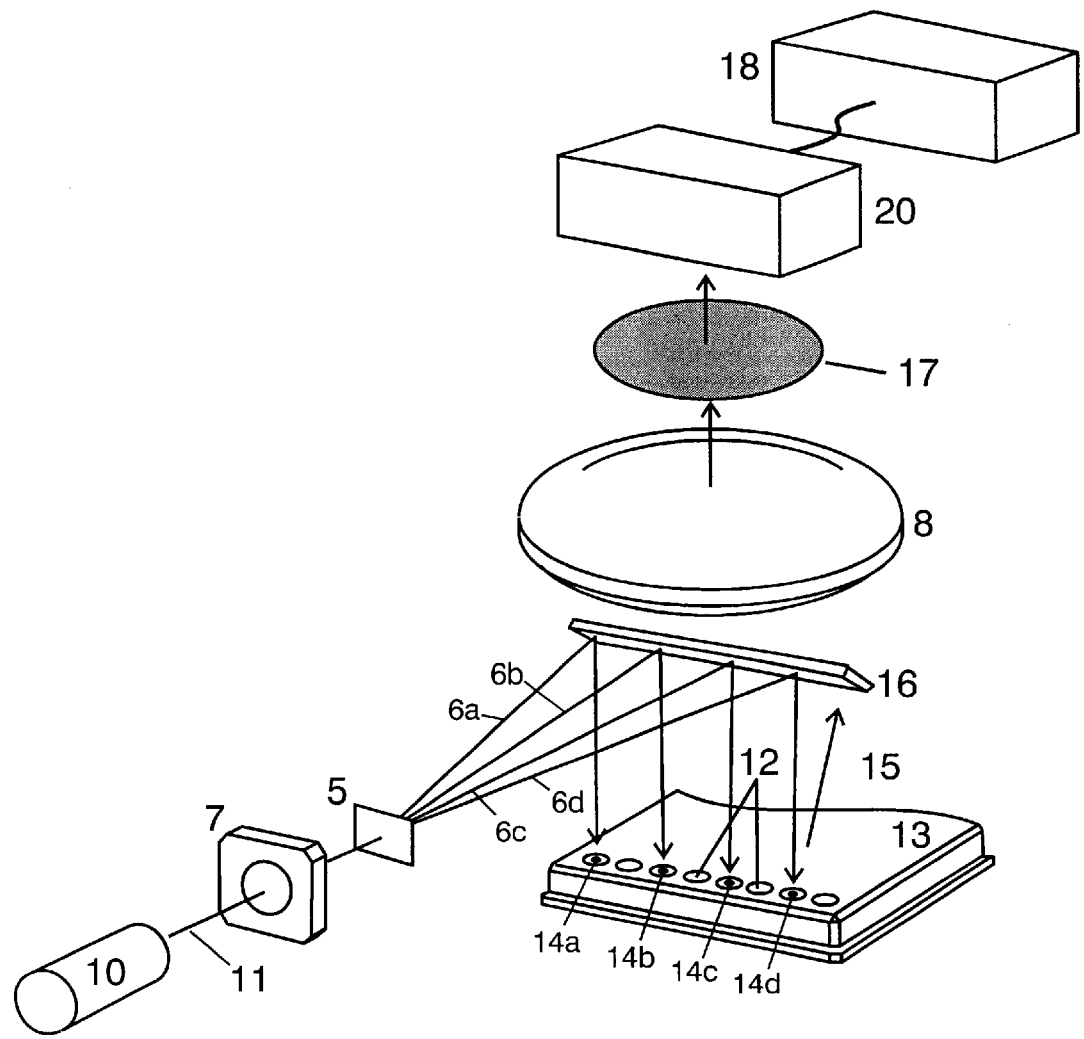
FIG. 1 shows an dual-band fluorescence detection instrument, including excitation source, sample chamber, collection optics, and detector module.

FIG. 1 shows an instrument in accordance with this invention. It consists of a laser source 10 emitting light 11. This light passes through optional diffractive optical element to produce multiple beams 6a–6d. The beams pass through optional polarization controller 7 that enables selection of the state of polarization of the beams as either h or v polarization. The beams reflect from mirror 16 and are presented to sample 12 in sample holder 13, where they illuminate spots 14a–14d which in turn emit fluorescent light that is captured by optics 8 that direct the light through barrier filter 17 to detector module 20 where the light from each spot is measured separately by readout electronics 18.

A full description of the illumination apparatus and its use for obtaining symmetric assessment of fluorescence polarization is provided in co-pending U.S. patent application Ser. No. 09/395,661, by the same inventor, entitled "Fluorescence Polarization Assay System and Method", the contents of which are hereby incorporated in full and made a part of this application. The illumination apparatus, polarization controller, and mirror and techniques described therein are appropriate for practicing the present invention, which provides for different detection module optics and operating modes.

Figure 2:
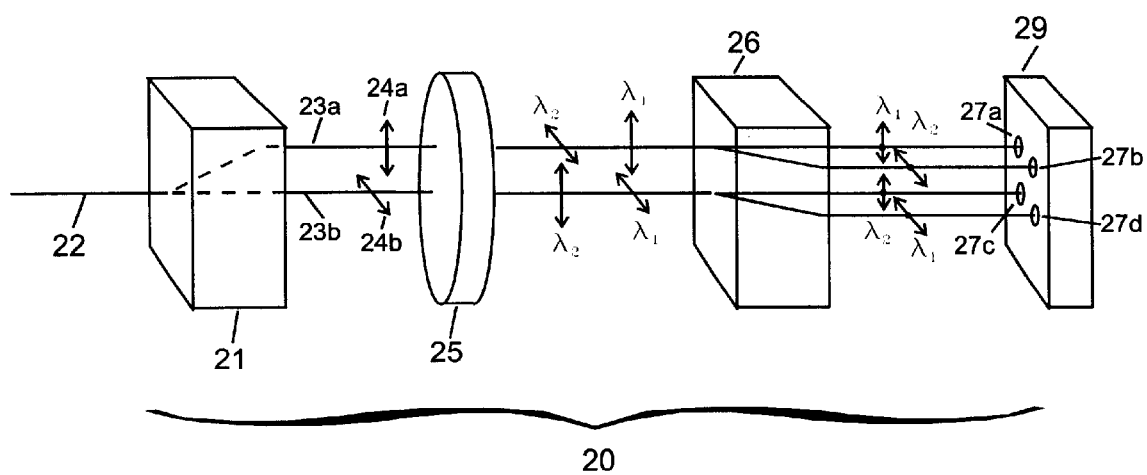
FIG. 2 shows a detector module for instantaneous dual-band measurements of fluorescence or fluorescence polarization.

FIG. 2 shows a preferred embodiment of the detection module 20 in detail. For clarity, we will trace out the passage of fluorescence emission from a single spot in the sample, although in practice there may be a single spot or many, depending on the illumination optics that are used. Detection module 20 consists of double-refractive element 21, which spatially separates incoming light 22 according to polarization state. Light that is v polarized is displaced in the y direction by element 21, while h polarized light is unaltered. The two polarized beams are shown as 23a and 23b, with polarization states indicated as 24a and 24b. They pass through a birefringent network 25 comprising one or more optical retarders in series, which alters the state of polarization to its complement, or not, depending on the wavelength. That is, certain wavelengths have their polarization completely transformed by network 25, while others are unchanged. We denote the wavelength band that is unaltered as $\lambda_1$ and the band that is changed as $\lambda_2$. The beams then encounter double refractive element 26, which spatially separates them according to polarization state. This element is like 21, but its axis is rotated by 90°, so light that is h polarized is displaced in the x direction by element 26, while v polarized light is unaltered. The result is that each spot in the sample generates four spots 27a–27d. Each spot corresponds to a particular combination of wavelength and polarization state when emitted by the sample, according to the table:

TABLE 1

Identification of spots (FIG. 2)

| Spot name | Polarization at sample | Wavelength band |
|---|---|---|
| 27a | v | $\lambda_1$ |
| 27b | v | $\lambda_2$ |
| 27c | h | $\lambda_1$ |
| 27d | h | $\lambda_2$ |

These are brought to a pixelated detector 29 such as a CCD detector, diode array, or multi-element photomultiplier tube (PMT), so the flux in each spot can be independently measured. The thicknesss of double-refractive elements 21 and 26 must be sufficient that the spots are fully separated in both x and y. When using multiple illumination spots, one must choose the spacing and location of spots at the sample so the various images of the sample spots produced by optics 8 do not overlap at detector 29 and may be measured independently. It is possible to illuminate multiple spots along a line, or in a two-dimensional grid pattern, if the detector is suitable.

The photodetector should have high quantum efficiency and low readout noise, in order to achieve high sensitivity. Suitable sources of CCD detectors include Hamamatsu Photonics (Bridgewater, N.J.) or Roper Scientific (Princeton, N.J.), and offer the benefit that by one can accommodate any spot pattern desired, just by addressing suitable regions in the image. Photodiode arrays offer lower cost and faster readout, and can be custom-made to fit the exact spot pattern produced by optics. Suitable sources include Hamamatsu Photonics, and Fermionics (Simi Valley, Calif.). Multi-element PMTs are available from Hamamatsu Photonics. Techniques for low-noise readout of all these elements are widely known in the art of electro-optical instrument design.

Figure 3:
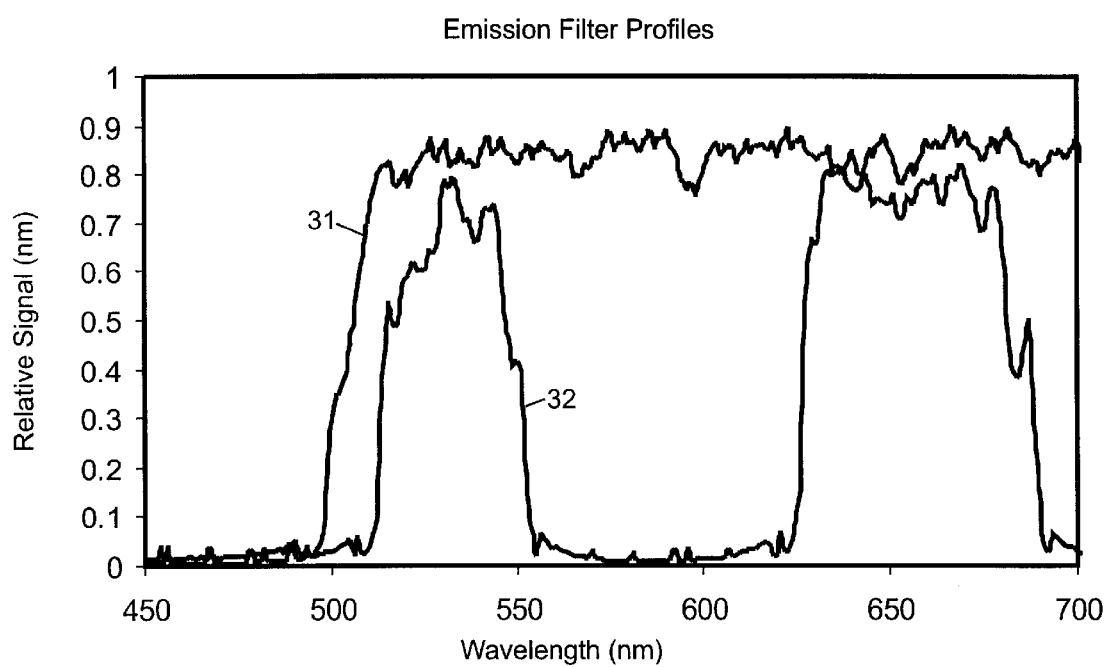
FIG. 3 shows the transmission vs. wavelength response for a cut-on filter and for a dual-band filter.

Barrier filter 17 may be a long-pass type, which transmits substantially all the light above a cut-on wavelength $\lambda_{co}$; or it may be a dual-band type with two well-defined transmission bands, centered on $\lambda_1$ and $\lambda_2$. The transmission vs. wavelength responses for such filters are shown in FIG. 3 as 31 for a long-pass type, and as 32 for a dual-band type. Such filters are widely used in fluorescence instruments, and are commercially available from firms such as Chroma (Brattleboro, Vt.) and Omega Optics (Brattleboro, Vt.).

The double-refractive elements can be a slab of calcite, rutile, or other optically anisotropic material. The crystal axis is preferably oriented at 45° to the propagation vector, so that the beam is deflected laterally, as is known in the art. Double refraction in optical media is explained in standard optics texts such as *Principles of Optics*, M. Born and E. Wolf, $7^{th}$ Ed., Cambridge University Press, NY, pp. 790–813 (1999). For calcite, the deflection is approximately 1/10 the thickness of the slab. Suitably oriented calcite slabs are available from Karl Lambrecht (Chicago, Ill.). Other materials by be equally suitable, based on the amount of double refraction, the availability of pieces in suitable size, as well as the usual design concerns of price, environmental ruggedness, and so on.

The spots will not come to focus at exactly the same plane after passing through a double-refractive element, due to the differential path length between rays that are displaced, and those that are not. It is possible to put an optical retarder in series with the double refractive element to correct for this focus shift. The amount of retardation should optimally be chosen to precisely match the differential path length encountered in the double refractive element. Such a compensating retarder can be made from a calcite slab whose crystal axis lies in the plane of the slab.

The choice to use a compensator for a double-refractive element, or not, will be dictated by the amount of differential path length involved and the optical system design. In an embodiment that utilizes two double-refractive elements, compensators could be used for both elements, none, or one. This will be dictated by factors such as the degree of tolerable focus shift for the optics involved, which may be determined by ray-tracing or other methods; by the cost and size required for the compensator(s); and other engineering design factors.

Figure 4:
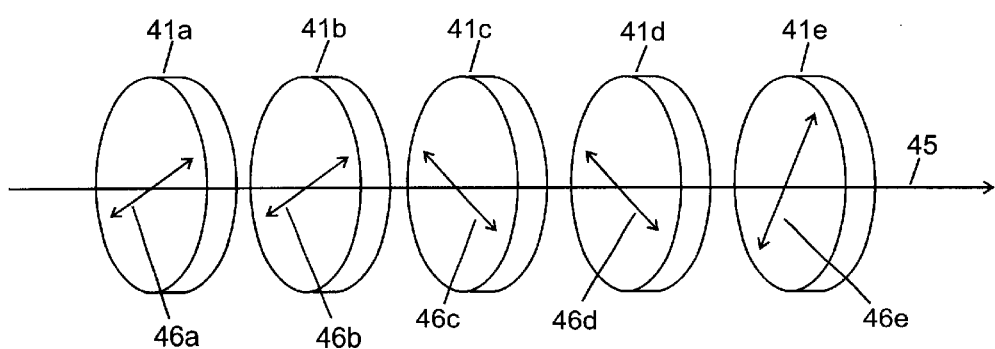
FIG. 4 shows a birefringent network for wavelength-dependent alteration of the state of polarization.

Construction of the birefringent network is shown in FIG. 4. It consists of 5 quartz waveplates shown as 41a through 41e, each with thickness of 30 mils (762 microns). Each waveplate is a disk having the specified thickness, cut from crystalline quartz such that the crystal axis lies in the plane of the disk within 5 minutes of arc. The quartz waveplates are mounted so that the crystal axes 46a–46e of each waveplate have a precisely known rotational orientation about the optical axis. The orientations of the five waveplates are {9.9°, 9.9°, −14.5°, −14.5°, 45°}, with respect to the x axis.

Figure 5:
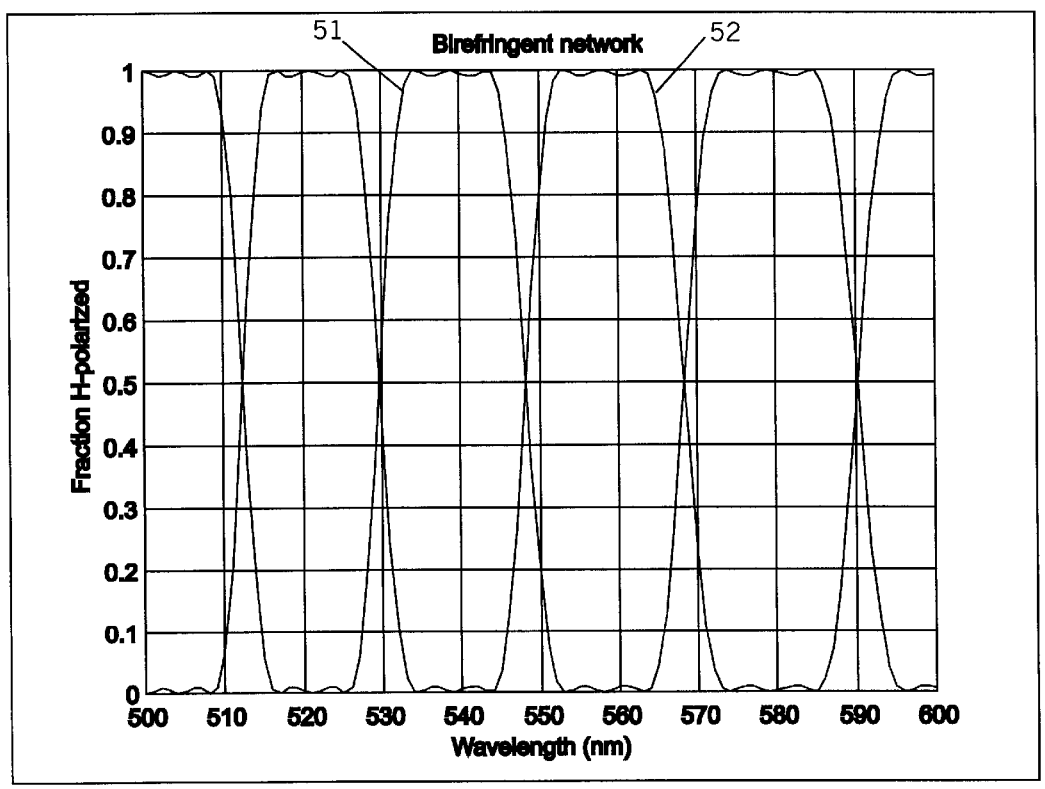
FIG. 5 shows the optical action of the birefringent network from FIG. 3, for incident light that is h-polarized.

This produces a wavelength-dependent alteration of polarization, as shown in FIG. 5. Curve 51 depicts the proportion of light that exits the network in h-polarization, as a function of wavelength, for h-polarized incident light. For example, at 538 nm nearly all the light exits in the network in the h-polarized state, while at 557 nm nearly all the light has been transformed to v-polarized state.

A birefringent network is lossless, so that fraction of light which is not h-polarized, exits the network in the v-polarized state. So curve 52, which is simply the complement of curve 51, depicts the fraction of light that exits the network in v polarization, for h-polarized incident light.

Similarly, for light that enters the network in the v-polarized state, curve 51 indicates the portion that exits the network still in the v-polarized state, while curve 52 indicates the portion that is transformed to the orthogonal, h-polarized state. Thus one can think of curve 51 as indicating the portion of light that exits the birefringent network with its polarization state unaltered, and curve 52 as indicating the portion that was transformed to the complementary state by the network. Viewed this way, curves 51 and 52 apply equally for h-polarized and v-polarized incident light.

The theory of birefringent networks, and the synthesis of networks to achieve a desired bandpass, is described in detail by E. O. Amman in "Synthesis of Optical Birefringent Networks", *Progress in Optics IX* (1971), pp. 123–177 (North-Holland, Amsterdam). This presents a general synthesis method from which one can determine how many retarders, of what thickness, and what orientation, are necessary to achieve a given bandpass. The general theory is supplemented by a description of a specialized family of filter designs with equal ripple in the passband and stopband, "Flat Passband Birefringent Wavelength Domain Multiplexer", W. J. Carlson and C. F. Buhrer, Electronics Letters pp. 106–107 (1987). Suitable quartz waveplates can be obtained from VLOC (Port Richey, Fla.).

Figure 6:
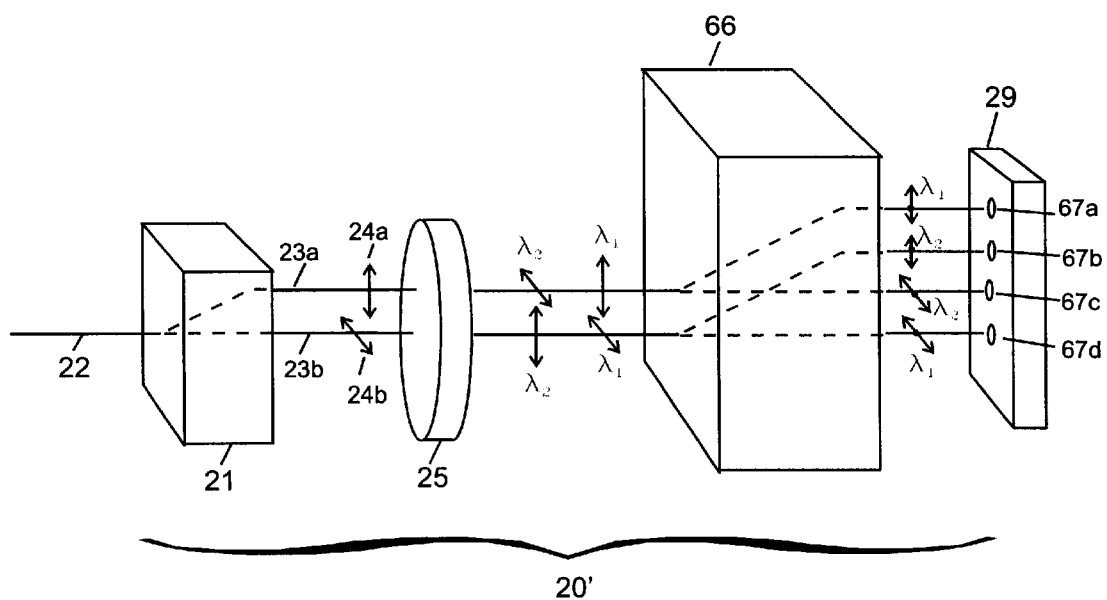
FIG. 6 shows another detector module for instantaneous dual-band measurements of fluorescence or fluorescence polarization.

It is not necessary that the first and second double-refractive crystal have their axes rotated by 90° from one another, although that is a suitable arrangement. The purpose of the double-refractive elements is to separate the light into four spots corresponding to the various combinations of wavelength band and polarization state at the sample. Another preferred embodiment that achieves this is shown in FIG. 6, tracing the rays for a single spot in the sample. Detection module 20' consists of double-refractive element 21, which spatially separates incoming light 22 according to polarization state. Light that is v polarized is displaced in the y direction by element 21, while h polarized light is unaltered. The two polarized beams are shown as 23a and 23b, with polarization states indicated as 24a and 24b. They pass through a birefringent network 25 and then encounter double refractive element 66, which spatially separates them according to polarization state. This element is like 21, but its thickness is twice as great so the amount of displacement for v-polarized light is twice that of element 21; once again, h-polarized light is unaltered. The result is that each spot in the sample generates four spots 67a–67d, this time in a line instead of a grid. Each spot corresponds to a particular combination of wavelength and polarization state when emitted by the sample, according to Table 2:

TABLE 2

Identification of spots (FIG. 6)

| Spot name | Polarization at sample | Wavelength band |
|---|---|---|
| 67a | v | $\lambda_1$ |
| 67b | h | $\lambda_2$ |
| 67c | v | $\lambda_2$ |
| 67d | h | $\lambda_1$ |

It would be possible to make element 66 half as thick as element 21, provided that the thicknesses are large enough to fully separate the light into distinct spots. The result will again be a set of four spots, although the location of spots 67b and 67c will be interchanged, as one can see by considering the displacements involved.

These embodiments illustrate many of the advantages of the present invention over the prior art. First, it measures both spectral bands simultaneously, so there is no sample aging or photobleaching between the measurement of the first and second band. Also, the exposures are taken under identical illumination. These are the predominant drift sources, so removing them greatly improves the precision with which one can measure spectral band ratios and the like.

However, unlike prior art dual-band devices which use two detectors, the present invention uses just one. This is superior in terms of cost, simplicity, size, and power consumption. Also, the readout stability is improved, since there is only one set of electronics rather than two, which may not track perfectly with age, temperature, and so on.

Further, it is practical to construct the present invention so as to look at multiple spots at once, by using a pixeleted detector such as a CCD or photodiode array. These multiple spots may be in a linear array, or a grid, according to the detector characteristics and the sample requirements. Measuring multiple spots at once further improves throughput for applications where one wishes to read a high volume of assays, such as high-throughput drug screening.

As the embodiments above illustrate, all the optics may be normal-incidence. This means the instrument is free of any polarization-dependent spectral shifts such as normally occur when using tilted dielectric surfaces. This is a vital when measuring samples having a polarization signature, but is valuable even when looking at nominally unpolarized samples, particularly for probes with a short Stokes shift.

One does not achieve optimum performance when the optical path contains off-axis dielectric coatings, because the response spectra differ for h- vs. v-polarized light. Specifically, the cut-on wavelength is not the same for both polarization states. So, in order to ensure both polarizations are adequately blocked, one must shift the passband longward slightly, which degrades collection efficiency.

Another powerful benefit of the invention is that all the light captured by the collection optics is utilized and measured at the detector. While the beam is divided according to wavelength, and further according to polarization state at the sample, all the resultant sub-beams are measured and contribute to the measurement statistics. This is in contrast to systems that use e.g. rotating polarizers or other lossy elements to measure polarization state. In practical terms, the double refractive elements and birefringent network can achieve efficiencies in excess of 95 percent.

Moreover, the invention provides an instantaneous measure of fluorescence polarization in each of the bands. It provides independent, accurate measures of the h-polarized and v-polarized portions of fluorescence emission. Such a measure gives superior precision to a time-series measurement of the two polarization components, for the same reasons given above in the context of the two spectral bands. And, once again, the use of a single detector in the present device is superior to use of two detectors in terms of cost, complexity, stability, and power consumption.

The ability to obtain fluorescence polarization data in two spectral bands, with high precision in each, is very powerful. Precision is one of the central FIGS. of merit in fluorescence polarization measurements, and also in most spectral band ratios. When performing dual-probe fluorescence polarization measurements, the requirement for precision in both bands is paramount. This is because there is inevitably spectral cross-talk between bands; that is, each probe will emit to some degree into both bands. This places more extreme signal-to-noise demands on the instrument, compared to a single-probe measurement. One must unmix the spectral cross-talk, and determine what proportion of the signal in each band came from which probe, in order to assess the degree of fluorescence polarization in each probe. Techniques for this unmixing and data analysis are taught in co-pending patent application "Multiple Label Fluorescence Polarization Assay System and Method", by the same inventor, filed the same day as this, the contents of which are hereby incorporated in full and made a part of this application.

Because of the precision it affords, the instrument of the present invention can be used to detect independent measurements of fluorescence in two labels per sample, even in the presence of cross-talk by probes into both bands.

This invention enables use of dual label fluorescence polarization measurements for single-nucleotide polymorphism (SNP) detection. No other instrument is capable of SNP measurement using fluorescence polarization assays. In this way the present invention makes possible for the first time an improved method of performing SNP assays, that takes advantage of the homogeneous, mix-and-read protocol of fluorescence polarization experiments. This greatly simplifies SNP assays, making them more economical and more reliable than was possible in the prior art using non fluorescent-polarization assays.

Figure 7:
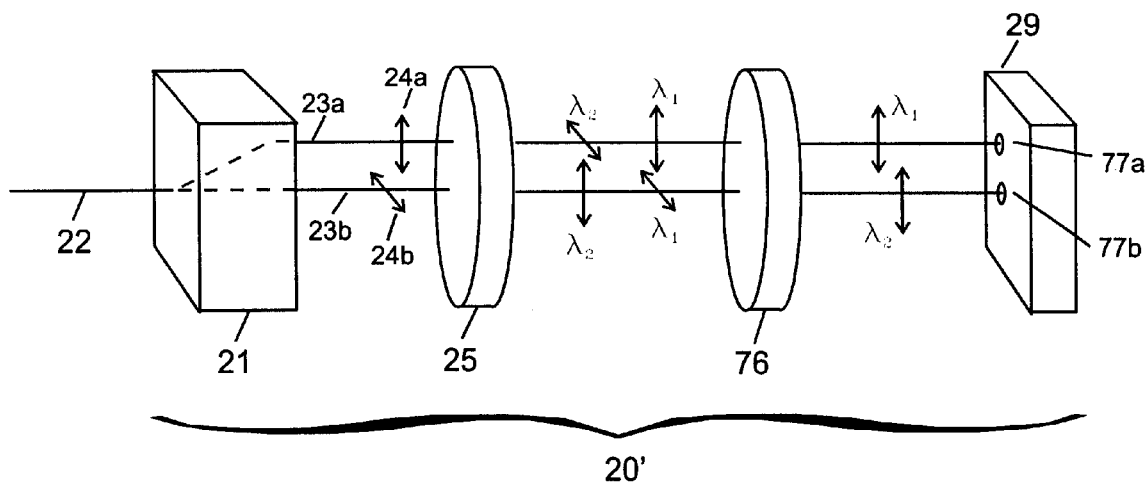
FIG. 7 shows a detector module for instantaneous dual-band measurements of fluorescence, using a linear polarizer.

FIG. 7 shows another preferred embodiment of the invention, which is useful for measurements where dual-band fluorescence is required, but there is no need to measure fluorescence polarization. It is essentially the embodiment of FIG. 2, except that the second double-refractive element has been replaced by a simple linear polarizer 76. Light 22 entering the detection module 20' is split according to polarization state into beams 23a and 23b. These pass through birefringent network 25 which alters the polarization, or not, according to wavelength band. These beams are received at polarizer 76, which transmits light of the one polarization and absorbs light of the orthogonal state. The transmitted light from the two spots falls on detector 29 and is measured.

Due to the action of the double refraction element and the birefringent network, the wavelength and sample polarization state for the spots are given by:

TABLE 3

Identification of spots (FIG. 7)

| Spot name | Polarization at sample | Wavelength band |
|---|---|---|
| 77a | v | $\lambda_1$ |
| 77b | h | $\lambda_2$ |

Figure 8:
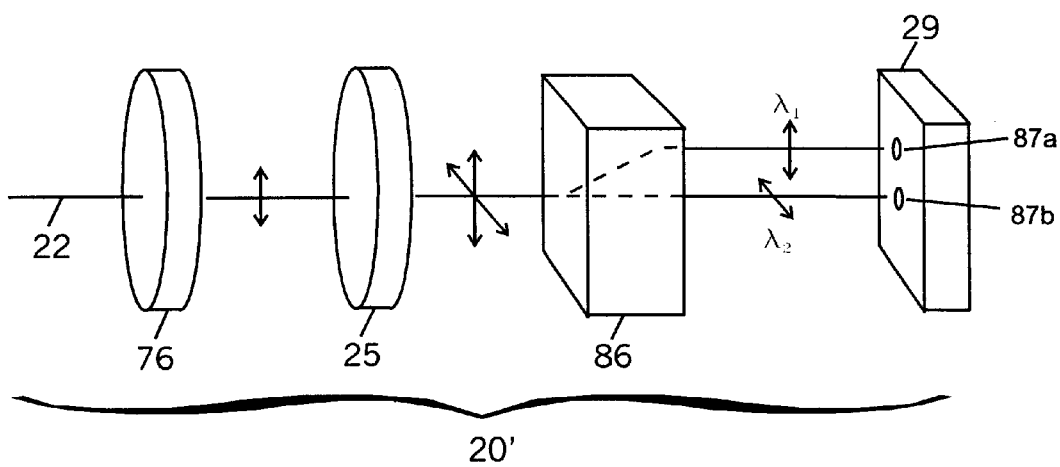
FIG. 8 shows another detector module for instantaneous dual-band measurement of fluorescence similar to that of FIG. 7, but with the components in different sequence.

The same elements can be arranged in a different order to yield another preferred embodiment of the invention. FIG. 8 shows a detection module 20' of this type, where the incoming light 22 first encounters a linear polarizer 76' oriented to transmit v-polarized light. The linear polarizer can be a piece of Polaroid HN-38S (Polaroid, Norwood, Mass.) or any other element that transmits substantially a single polarization of light in the wavelength range of interest. A single beam passes through birefringent network 25, which alters the state of polarization, or not, according to the wavelength involved. The beam then encounters a double refractive element 86, which spatially displaces v-polarized light while transmitting h-polarized light without displacement. The result are two spots, 87a and 87b, for which the wavelength and sample polarization state are given by:

TABLE 4

Identification of spots (FIG. 8)

| Spot name | Polarization at sample | Wavelength band |
|---|---|---|
| 87a | v | $\lambda_1$ |
| 87b | v | $\lambda_2$ |

Considering the embodiments of FIGS. 7 and 8, these provide many of the same benefits discussed earlier in connection with the embodiments of FIGS. 2 and 6, while replacing a double-refractive element with a more economical linear polarizer. They provide a dual-band fluorescence measurement, with high precision. Again, use of a simultaneous measurement eliminates sample aging effects, and the identical exposure conditions ensure freedom from lamp flicker or drift. However, only a single detector is needed, with savings in cost, size, and power dissipation. The instrument can be designed so it reads several spots at once, by illuminating several spots on the sample and using a detector with suitable pixels. Versions with 16 spots have been made, and more are possible if desired. Throughput is increased directly by to the parallelism inherent in reading several spots at once, so one can build embodiments of the invention suitable for use in very-high-throughput drug screening and clinical applications. The design is free from tilted dielectric surfaces, so one can operate at short Stokes shifts without compromise.

This design does not provide fluorescence polarization data for each band, and is suited for applications where one wishes to measure fluorescence intensity in one or two bands, or to measure ratios thereof. It is interesting to note that the design of FIG. 7 derives its reading of $\lambda_1$ from the v-polarized sample emission, while it derives its reading of $\lambda_2$ from the h-polarized sample emission. In contrast, the design of FIG. 8 derives both the reading of $\lambda_1$ and $\lambda_2$ from the v-polarized sample emission. So, they will react differently from one another when faced with samples that are partially polarized in a way that varies with wavelength band. Based on Tables 3 and 4, one can predict how each instrument would react, and it may be possible to use one instrument, or the other, successfully with samples of this type. However, it may be preferable, when faced with a sample having complex spectro-polarimetric output, to use the apparatus of FIG. 2 or FIG. 6, which yield full and accurate data on both spectral band and polarization within the band.

Figure 9:
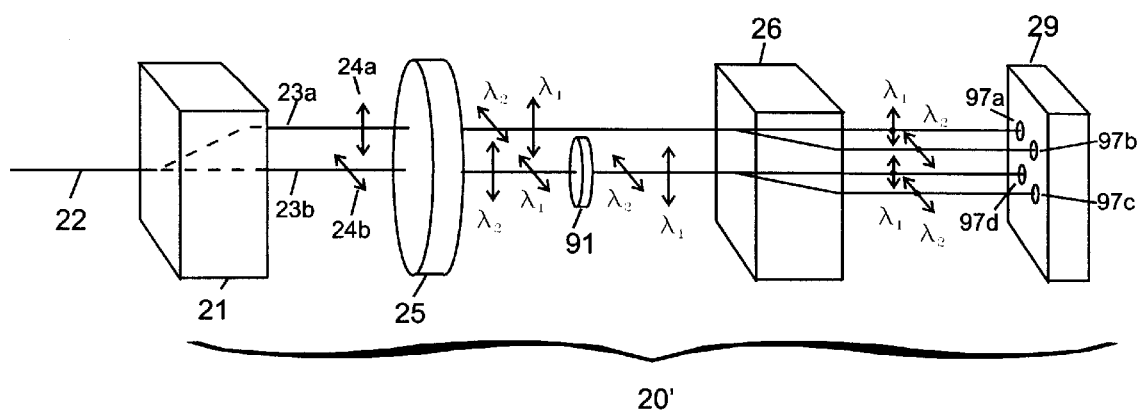
FIG. 9 shows another detector module optimized for high-speed readout of dual-band fluorescence measurements.

FIG. 9 shows yet another preferred embodiment, which is optimized for high-speed dual-band fluorescence measurements. It comprises the same elements as shown in FIG. 2, with an optical retarder 91 placed between the first and second double-refractive elements. This is inserted into only one of the two beams. If desired, an optical rotator or twisted nematic element can be used, or indeed any optical component that transforms the state of polarization to the complementary state. The result of adding this element is that the spot which used to be displaced at double-refractive element 26, now has the orthogonal polarization and passes through without displacement; and the spot was not displaced before, now is. Consequently, the spot identifications change to:

TABLE 5

Identification of spots (FIG. 9)

| Spot name | Polarization at sample | Wavelength band |
|---|---|---|
| 97a | v | $\lambda_1$ |
| 97b | v | $\lambda_2$ |
| 97c | h | $\lambda_2$ |
| 97d | h | $\lambda_1$ |

This means that the spots that share a common wavelength are now spatially adjacent, rather than diagonally arranged from one another. If the detector pixels are suitably chosen, it is practical that both spots for a given wavelength can be captured by a single pixel (in the case of a photodiode array or pixelated PMT); or by a column of pixels in the case of a CCD camera. This improves readout speed for two reasons. First, the electronics readout speed is increased if one can bin all pixels in a CCD array; or if one can replace a CCD array with a photodiode array. This is due simply to the circuitry involved, as is known in the electronics art. Second, the optical arrangement delivers all the flux into a single region for concurrent readout. This means that the flux from both spots contribute to the signal, and signal-to-noise is doubled for a given exposure (for a fixed noise level); put conversely, one can attain a given signal-to-noise with only half the exposure time. This further enables high measurement speed, which is valuable in studies of membrane potential, cell dynamics, and the like.

If the polarization transforming element 91 is a liquid crystal cell or other electro-optic device, it is possible to switch the spot assignments dynamically. By comparing measurements made under both conditions one can determine the relative responsivity of the different pixels of the detector thus interchanged, at each wavelength band. This is valuable for in-situ calibration and instrument characterization. If element 91 is pixelated so that one may change the state of polarization for one beam passing through it, or both, or none, then may interchange either pair of spots for this purpose, or for any other reason.

Figure 10:
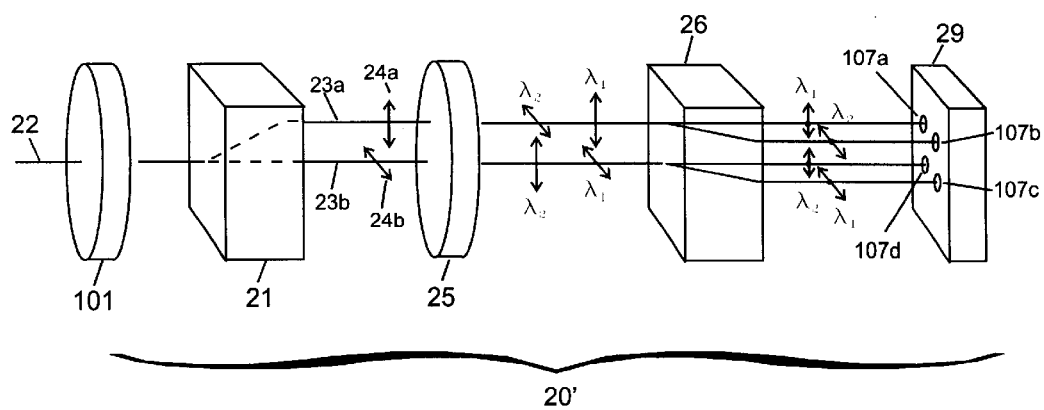
FIG. 10 shows another detector module for instantaneous dual-band measurements of fluorescence or fluorescence polarization, which enables interchanging the arrangement of sample spots at the detector.

This principle can be exploited with a polarization rotating element 101 placed before the first double refractive element, as shown in FIG. 10. Again, the rest of the apparatus is the same as was depicted in FIG. 2. The element 101 may again be a retarder, rotator, twisted nematic cell, or any other element that is capable of transforming the state of polarization to its complement. Since there is only one beam per sample spot at this point in the optical path, element 101 affects all light being measured for that sample. Adding such an element means that sample emissions having a polarization which previously were displaced at element 21', are now transmitted without displacement; and emissions having a polarization which was previously undisplaced at element 21' are now displaced. The resulting table is:

TABLE 6

Identification of spots (FIG. 10)

| Spot name | Polarization at sample | Wavelength band |
|---|---|---|
| 107a | h | $\lambda_1$ |
| 107b | h | $\lambda_2$ |
| 107c | v | $\lambda_1$ |
| 107d | v | $\lambda_2$ |

If element 101 is a liquid crystal cell or other electro-optic element, it is possible to take readings in one setting where the polarization is rotated; then to take readings in a setting where the polarization is unaffected by element 101. Since this re-arranges what pixel on the detector receives which signal, one can use this measurement set to characterize the relative response of the detector at the various pixels involved.

Polarization rotating elements may be placed in front of the first double-refractive element and between the first and second double-refractive elements, and used in concert for purposes of calibration or characterization of the instrument and assay. The determination of what spot comprises a given wavelength and sample emission state of polarization, can be determined by standard optical methods together with the teaching given above.

The principles of this invention illustrated in the above embodiments may be combined with one another, or with the teachings in my co-pending patents incorporated herein, as described above and in other ways that will be evident to those skilled in the arts of instrument design and polarized light. Similarly, use of optical elements or algorithms that achieve substantially the same results as the examples and embodiments shown here, may be undertaken with success, and the choice to do so will be dictated by engineering consideration, including such factors such as economy, size, ease-of-integration, computation speed, simplicity, and the like.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. An apparatus for at least one of fluorescence detection and fluorescence measurement of fluorescence intensity, comprising:
   at least one light emitting source for emitting at least one beam of light for illuminating at least one sample for effecting emissions of fluorescent light from said at least one sample, said emitted fluorescent light comprised at least of first and second predetermined spectral bands; and
   a detector positioned for receiving the emitted fluorescent light from the at least one sample, for spatially separating the emitted fluorescent light into component beams based at least on spectral band, and for detecting an emission flux of at least one component beam, said detector, comprising:
      a polarization-sensitive optical element for receiving the emitted fluorescent light, for transmitting the received light in the tint predetermined spectral band therethrough without alteration, and for transmitting the received light in the second predetermined spectral band therethrough such that its polarization state upon exiting the polarization-sensitive optical element is the complement of its polarization state before entering the polarization-sensitive optical element;
      a double refractive element positioned in optical series either before or after the polarization-sensitive optical element, said double refractive element for separating light incident thereon into spatially distinct beams according to polarization state, wherein
         if positioned before the polarization-sensitive optical element, said double-refractive element receives the emitted fluorescent light and spatially separates the received light into two beams according to polarization state; or
         if positioned after the polarization-sensitive optical element, said double-refractive element spatially separates the component beams of each set according to polarization state; and
      a photodetector for detecting the emission flux of at least one component beam received after passing through both said polarization-sensitive element and said double refractive element.

2. The apparatus as recited in claim 1, wherein the detector spatially separates the emitted fluorescent light into component beams based on both spectral band and polarization state of said component beams as emitted from the at least one sample.

3. The apparatus as recited in claim 1, wherein the photodetector is a pixelated detector comprising one of a diode array, a multi-element photomultiplier tube (PMT), and a charge-coupled device (CCD).

4. The apparatus as recited in claim 1, wherein the double-refractive element is one is of a slab of calcite, a slab of rutile, and a slab of another optically anisotropic material.

5. The apparatus as recited in claim 1, wherein the polarization-sensitive optical element comprises a stacked plurality of birefringent waveplates with each waveplate oriented in a predetermined direction.

6. The apparatus as recited in claim 5, wherein the stacked plurality of birefringent waveplates comprises:
   a first quartz waveplate cut from crystalline quartz such that the rotational orientation of its crystal axis about the optical axis is 9.9°;
   a second quartz waveplate cut from crystalline quartz such that the rotational orientation of its crystal axis about the optical axis is 9.90°;
   a third quartz waveplate cur from crystalline quartz such that the rotational orientation of its crystal axis about the optical axis is −14.50°;
   a fourth quartz waveplate cut from crystalline quartz such that the rotational orientation of its crystal axis about the optical axis is −14.50°; and
   a fifth quartz waveplate cut from crystalline quartz such that its rotational orientation about the optical axis is 45°;
   wherein the crystal axis angles are specified relative to the vector describing the beam separation produced by said double refractive element.

7. The apparatus as recited in claim 1, wherein the detector comprises, in optical series;
   said double-refractive element as a first double-refractive element for spatially decomposing the emitted fluorescent light into a first and second orthogonally polarized beams, an axis of said first double-refractive element being oriented so that the first and second beams are displaced from and parallel to each other;
   said polarization-sensitive optical element positioned for receiving the first and second beams, for decomposing the first beam into a third and fourth orthogonally polarized beams, and for decomposing the second beam into a fifth and sixth orthogonally polarized beams, wherein the fourth and sixth beams carry the first predetermined spectral band, and the third and fifth beams carry the second predetermined spectral band;
   a second double-refractive element positioned for receiving the third, fourth, fifth, and sixth beams and for spatially separating the third and fourth beams and the fifth and sixth beams according to their respective polarizations, an axis of said second double-refractive element being oriented so that the fourth and fifth beams are displaced from and parallel to the third and sixth beams, respectively; and
   said photodetector positioned for receiving the third, fourth, fifth, and sixth beams at four spatially distinct spots, wherein the fourth and sixth beams comprise light in the first predetermined spectral baud and the third and fifth beams comprise light in the second predetermined spectral band, and wherein the third and fifth beams have polarizations orthogonal to the fourth and sixth beams, respectively.

8. The apparatus as recited in claim 7, wherein an optical axis of said first double-refractive element is rotated by 90° relative to an optical axis of said second double-refractive element so that the four spatially distinct spots form a grid pattern.

9. The apparatus as recited in claim 7, wherein an optical axis of said first double-refractive element is oriented similarly to an optical axis of said second double-refractive element so that the four spatially distinct spots form a line.

10. The apparatus as recited in claim 7, wherein the detector further comprises:
   a polarization rotating optical element for changing positions of the four spatially distinct spots on said photodetector.

11. The apparatus as recited in claim 10, wherein, in order to reverse the position on said photodetector of the spatially distinct spot formed by the fifth beam with the spatially distinct spot formed by the sixth beam, the polarization rotating optical element is positioned in optical series between said polarization-sensitive optical element and said second double refractive element, wherein said polarization rotating optical is for receiving the fifth and sixth orthogonally polarized beams and changing the polarization of the fifth and sixth beams to their respective complementary states.

12. The apparatus as recited in claim 10, wherein, in order to reverse the positions on said photodetector of the spatially distinct spots formed by the third and fourth beams with the positions of the spatially distinct spots formed by the sixth and fifth beams, respectively, the polarization rotating optical element is positioned in optical series before said first double refractive element, wherein said polarization rotating optical is for receiving the emitted fluorescent light and changing the polarization of each of its component beams to its complementary state.

13. The apparatus as recited in claim 10, wherein said polarization rotating optical element is one of an optical retarder, polarization rotator, or twisted nematic liquid crystal cell.

14. The apparatus as recited in claim 1, wherein the detector comprises, in optical series:
   said double refractive element as a first double-refractive element for spatially decomposing the emitted fluorescent light into a first and second orthogonally polarized beams, an axis of said first double-refractive element being oriented so that the first and second beams are displaced from and parallel to each other;
   said polarization-sensitive optical element positioned for receiving said first and second beams, decomposing said first beam into a third and fourth orthogonally polarized beams, and decomposing said second beam into a fifth and sixth orthogonally polarized beams, and wherein said fourth and sixth beams carry the first predetermined spectral band, said third and fifth beams carry the second predetermined spectral band, said third and sixth beams have a first polarization, and said fourth and fifth beams have a second polarization orthogonal to the first polarization;
   a linear polarizer positioned for receiving the third, fourth, fifth, and sixth beams, for absorbing the third and sixth beams having said first polarization, and for transmitting the fourth and fifth beams having said second polarization; and
   said photodetector positioned for receiving the fourth and fifth beams at two spatially distinct spots, wherein the fourth beam comprises light in the first predetermined spectral band, and the fifth beam comprises light in the second predetermined spectral band.

15. The apparatus as recited in claim 1, wherein the detector comprises, in optical series:
   a linear polarizer positioned for receiving the emitted fluorescent light, for absorbing a component of said emitted fluorescent light with a first polarization state, and for transmitting a component of said emitted fluorescent light with a second polarization state, wherein the first polarization state is orthogonal to the second polarization state;
   said polarization-sensitive optical element positioned for receiving the transmitted component with a second polarization state, and for decomposing the transmitted component into a first beam carrying a first predetermined spectral band with a third polarization and a second beam carrying a second predetermined spectral band with a fourth polarization orthogonal to said third polarization;
   said double-refractive element positioned for receiving said first and second beams and for spatially separating the first beam and the second beam according to their respective polarizations, an axis of said first double-refractive element being oriented so that the first and second beams are displaced from and parallel to each other; and
   said photodetector positioned for receiving the first and second beams at two spatially distinct spots, wherein the first beam comprises light in the first predetermined spectral band, and the second beam comprises light in the second predetermined spectral band.

16. The apparatus as recited in claim 1, further comprising:
   at least one polarization controller disposed between said at least one light emitting source and said at least one sample for selecting a state of polarization of the at least one beam of light for illuminating the at least one sample.

17. The apparatus as recited in claim 1, further comprising:
   at least one diffractive optical element disposed between said at least one light emitting source and said at least one sample for splitting the at least one beam of light for illuminating the at least one sample into multiple beams.

18. The apparatus as recited in claim 17, wherein the at least one sample is on a multiwell plate and said multiple beams illuminate said plurality of samples.

19. The apparatus as recited in claim 1, further comprising:
   at least one mirror positioned to reflect the at least one beam of light for illuminating the at least one sample onto the at least one sample.

20. The apparatus as recited in claim 1, further comprising:
   an optical element disposed between said at least one sample and said detector for receiving the emitted fluorescent light and resolving said received light into at least one resolved beam, and wherein said resolved beam is incident on the detector.

21. The apparatus as recited in claim 1, further comprising:
   at least one filter disposed between said at least one sample and said detector for receiving the emitted fluorescent light, transmitting at least the first and second predetermined spectral bands, and filtering out remaining spectral bands.

22. The apparatus as recited in claim 21, wherein the at least one filter filters out one of (a) all wavelengths below a cut-on wavelength and (b) all wavelengths outside of two or more spectral bands.

23. The apparatus as recited in claim 1, wherein the at least one light-emitting source is at least one laser.

24. An apparatus for at least one of fluorescence detection and fluorescence measurement of fluorescence intensity, comprising:

at least one light emitting source for emitting at least one beam of light for illuminating at least one sample for effecting emissions of fluorescent light from said at least one sample, said emitted fluorescent light comprised at least of first and second predetermined spectral bands; and a detector positioned for receiving the emitted fluorescent light from the at least one sample, for spatially separating the emitted fluorescent light into four component beams based on spectral band and polarization state, and for detecting an emission flux of each of the four component beams, said detector comprising, in optical series:

a first double refractive element for spatially separating the emitted fluorescent light into two spatially distinct beams according to polarization state;

a polarization-sensitive optical element for receiving the two spatially distinct beams and decomposing each of them into a set of two component beams, one component beam carrying the first predetermined spectral band and the other component beam carrying the second predetermined spectral band, wherein the two component beams have orthogonal polarization states but share the same optical path;

a second double refractive element for receiving the two sets of component beams and for spatially separating the component beams of each set according to polarization state; and a photodetector for receiving the four spatially distinct component beams and for detecting an emission flux of each.

25. The apparatus as recited in claim 24, wherein the photodetector is a pixelated detector comprising one of a diode array, a multi-element photomultiplier tube (PMT), and a charge-coupled device (CCD).

26. The apparatus as recited in claim 24, wherein the double-refractive element is one of a slab of calcite, a slab of rutile, and a slab of another optically anisotropic material.

27. The apparatus as recited in claim 24, wherein the polarization-sensitive optical element comprises a stacked plurality of birefringent waveplates with each waveplate oriented in a predetermined direction.

28. The apparatus as recited in claim 27, wherein the stacked plurality of birefringent waveplates comprises;

a first quartz waveplate cut from crystalline quartz such that the rotational orientation of its crystal axis about the optical axis is 9.9°;

a second quartz waveplate cut from crystalline quartz such that the rotational orientation of its crystal axis about the optical axis is 9.9°;

a third quartz waveplate cut from crystalline quartz such that the rotational orientation of its crystal axis about the optical axis is −14.5°;

a fourth quartz waveplate cut from crystalline quartz such that the rotational orientation of its crystal axis about the optical axis is −14.5°; and a fifth quartz waveplate cut from crystalline quartz such that its rotational orientation about the optical axis is 45°;

wherein the crystal axis angles are specified relative to the vector describing the beam separation produced by said double refractive element.

29. The apparatus as recited in claim 24, wherein an optical axis of said first double-refractive element is rotated by 90° relative to an optical axis of said second double-refractive element so that the four spatially distinct spots form a grid pattern.

30. The apparatus as recited in claim 24, wherein an optical axis of said first double-refractive element is oriented similarly to an optical axis of said second double-refractive element so that the four spatially distinct spots form a line.

31. The apparatus as recited in claim 24, wherein the detector further comprises;

a polarization rotating optical element for changing positions of the four spatially distinct spots on said photodetector.

32. The apparatus as recited in claim 31, wherein, in order to reverse the position an said photodetector of the spatially distinct spot formed by the fifth beam with the spatially distinct spot formed by the sixth beam, the polarization rotating optical element is positioned in optical series between said polarization-sensitive optical element and said second double refractive element, wherein said polarization rotating optical is for receiving the fifth and sixth orthogonally polarized beams and changing the polarization of the fifth and sixth beams to their respective complementary states.

33. The apparatus as recited in claim 31, wherein, in order to reverse the positions on said photodetector of the spatially distinct spots formed by the third and fourth beams with the positions of the spatially distinct spots formed by the sixth and fifth beams, respectively, the polarization rotating optical element is positioned in optical series before said first double refractive element, wherein said polarization rotating optical is for receiving the emitted fluorescent light and changing the polarization of each of its component beams to its complementary state.

34. The apparatus as recited in claim 31, wherein said polarization rotating optical element is one of an optical retarder, polarization rotator, or twisted nematic liquid crystal cell.

* * * * *